US011053492B2

(12) United States Patent
Brangwynne et al.

(10) Patent No.: US 11,053,492 B2
(45) Date of Patent: Jul. 6, 2021

(54) DISORDERED PROTEIN-BASED SEEDS FOR MOLECULAR CLUSTERING

(71) Applicant: The Trustees of Princeton University, Princeton, NJ (US)

(72) Inventors: Cliff Brangwynne, Hopewell, NJ (US); Dan Bracha, Princeton, NJ (US)

(73) Assignee: THE TRUSTEES OF PRINCETON UNIVERSITY, Princeton, NJ (US)

( * ) Notice: Subject to any disclaimer, the term of this patent is extended or adjusted under 35 U.S.C. 154(b) by 0 days.

(21) Appl. No.: 16/704,115

(22) Filed: Dec. 5, 2019

(65) Prior Publication Data
US 2020/0095569 A1    Mar. 26, 2020

Related U.S. Application Data

(62) Division of application No. 15/618,361, filed on Jun. 9, 2017, now Pat. No. 10,538,756.

(60) Provisional application No. 62/467,362, filed on Mar. 6, 2017.

(51) Int. Cl.
*C12N 11/02* (2006.01)
*C07K 1/14* (2006.01)

(52) U.S. Cl.
CPC .............. *C12N 11/02* (2013.01); *C07K 1/14* (2013.01); *C07K 2319/00* (2013.01); *C07K 2319/50* (2013.01); *C07K 2319/60* (2013.01); *C07K 2319/735* (2013.01)

(58) Field of Classification Search
CPC ....................... C12N 9/0061; C12Y 110/03002
See application file for complete search history.

(56) References Cited

U.S. PATENT DOCUMENTS 7,097,841 B2    8/2006 Carter et al.

OTHER PUBLICATIONS

Janmey et al. 2003; Assembly and structure of neurofilaments. Current Opinion in Colloid and Interface Science. 8: 40-47.*
Tompa 2013; Hydrogel formation by multivalent IDPs A reincarnation of the macrotrabecular lattice? Intrinsically disordered Proteins. 1: e24068, pp. 1-8.*
Mi et al. 2006; Self-assembling protein hydrogels with modular integrin binding domains. Biomacromolecules. 7: 38-47.*
Mao et al. "Biogenesis and function of nuclear bodies", Trends in Genetics, vol. 27, No. 8, Aug. 2011.
Anderson et al. "RNA granules: post-transcriptional and epigenetic modulators of gene expression" Nature reviews Molecular cell biology, vol. 10, No. 6, pp. 430-436, Jun. 2009.
Buchan et al. "Eukaryotic Stress Granules: The Ins and Outs of Translation", Molecular Cell. 36(6):932-41, Dec. 24, 2009.
Handwerger et al. "Subnuclear organelles: new insights into form and function", Trends in Cell Biology, vol. 16, No. 1, Jan. 2006.
Li et al. "Stress granules as crucibles of ALS pathogenesis", The Journal of Cell Biology, 201 (3): 361, Apr. 29, 2013.
Ramaswami et al. "Altered Ribostasis: RNA-Protein Granules in Degenerative Disorders", Cell 154, pp. 727-736, Aug. 15, 2013.
Phair et al. "High mobility of proteins in the mammalian cell nucleus", Nature, vol. 404, pp. 604-609, Apr. 6, 2000.
Brangwynne et al. "Germline P Granlues Are Liquid Droplets That Localize by Controlled Dissolution/Condensation" Science, vol. 324, pp. 1729-1733, Jun. 26, 2009.
Brangwynne et al. "Active liquid-like behavior of nucleoli determines their size and shape in Xenopus laevis oocytes", Proc Natl Acad Sci U S A. 108(11):4334-9, Mar. 15, 2011.
Feric et al. "A nuclear F-actin scaffold stabilizes ribonucleoprotein droplets against gravity in large cells", Nature Cell Biology, vol. 15, No. 10, Oct. 2013.
Ishimoto et al. "Critical Behavior of a Binary Mixture of Protein and Salt Water", Physical Review Letters, vol. 39, No. 3, pp. 474-477, Aug. 22, 1977.
Peter G. Vekilov "Phase transitions of folded proteins", The Royal Society of Chemistry, Soft Matter, 6, 5254-5272, Jun. 30, 2010.
Weber et al. "Inverse Size Scaling of the Nucleolus by a Concentration-Dependent Phase Transition", Current Biology 25, 641-646, Mar. 2, 2015.
Nott et al. "Phase Transition of a Disordered Nuage Protein Generates Environmentally Responsive Membraneless Organelles", Molecular Cell 57, 936-947, Mar. 5, 2015.
Wippich et al. "Dual Specificity Kinase DYRK3 Couples Stress Granule Condensation/Dissolution to mTORC1 Signaling", Cell 152, 791-805, Feb. 14, 2013.
Molliex et al. "Phase Separation by Low Complexity Domains Promotes Stress Granule Assembly and Drives Pathological Fibrillization", Cell 163, 123-133, Sep. 24, 2015.

(Continued)

*Primary Examiner* — Karen Cochrane Carlson
(74) *Attorney, Agent, or Firm* — Meagher Emanuel; Laks Goldberg & Liao, LLP.

(57) ABSTRACT

A system and method for reversibly controlling clustering of proteins around an engineered multivalent nucleus is disclosed. The system and method utilize clustering, which may be controlled by light activation or deactivation. The system and method enable the spatiotemporal control of protein supramolecular assemblies, including liquid-like droplets under some conditions, and solid-like gels under other conditions. The system and method can be utilized for segregating or locally concentrating desired proteins and/or RNA in cells or cell lysate, which may be useful for protein purification purposes, or for assembling single or multiple membraneless bodies within specific sub-regions of the cells. These synthetically assembled bodies may recruit both transgenic and endogenic proteins and other biomolecules, thus can be linked to affect and even trigger a plethora of cellular processes, including both physiological and pathological (e.g., protein aggregation) processes.

16 Claims, 10 Drawing Sheets
Specification includes a Sequence Listing.

(56) References Cited

OTHER PUBLICATIONS

Li et al. "Phase transitions in the assembly of multivalent signalling proteins", Nature, vol. 483, pp. 336-341, Mar. 15, 2012.

Sudeep Banjade Michael K Rosen: "Phase transitions of multivalent proteins can promote clustering of membrane receptors", Biophysics and Structural Biology Cell Biology, eLife 2014;3:e04123, Oct. 16, 2014.

Elbaum-Garfinkle et al. "The disordered P granule protein LAF-1 drives phase separation into droplets with tunable viscosity and dynamics", PNAS, vol. 112, No. 23, pp. 7189-7194, Jun. 9, 2015.

Lin et al. "Formation and Maturation of Phase-Separated Liquid Droplets by RNA-Binding Proteins", Molecular Cell 60, pp. 208-219, Oct. 15, 2015.

Zhang et al. "RNA Controls PolyQ Protein Phase Transitions", Molecular Cell 60, 220-230, Oct. 15, 2015.

Weber et al. "Getting RNA and Protein in Phase", Cell 149, pp. 1188-1191, Jun. 8, 2012.

Xiang et al. "The LC Domain of hnRNPA2 Adopts Similar Conformations in Hydrogel Polymers, Liquid-like Droplets, and Nuclei", Cell 163, 829-839, Nov. 5, 2015.

Patel et al. "A Liquid-to-Solid Phase Transition of the ALS Protein FUS Accelerated by Disease Mutation", Cell 162, 1066-1077, Aug. 27, 2015.

Toettcher et al. "Light-based feedback for controlling intracellular signaling dynamics", Nature Methods, vol. 8, No. 10, pp. 837-841, Oct. 2011.

Kennedy et al. "Rapid blue-light-mediated induction of protein interactions in living cells", Nature Methods, vol. 7, No. 12, pp. 973-841, Dec. 2010.

Levskaya et al. "Spatiotemporal control of cell signalling using a light-switchable protein interaction", Nature, vol. 161, pp. 997-1001, Oct. 15, 2009.

Bugaj et al. "Optogenetic protein clustering and signaling activation in mammalian cells", Nature Methods, vol. 10, No. 3, pp. 249-254, Mar. 2013.

Lee et al. "Reversible protein inactivation by optogenetic trapping in cells", Nature Methods, vol. 11, No. 6, pp. 633-638, Jun. 2014.

Taslimi et al. "An optimized optogenetic clustering tool for probing protein interaction and function", Nature Communications |DOI: 10.1038/ncomms5925, 2014.

G. Bellapadrona, M. Elbaum, "Supramolecular protein assemblies in the nucleus of human cells." Angew. Chem., 126 (6), pp. 1560-1563, 2014.

* cited by examiner

DISORDERED PROTEIN-BASED SEEDS FOR MOLECULAR CLUSTERING

CROSS-REFERENCE TO RELATED APPLICATIONS

This application claims priority to U.S. Provisional Application No. 62/467,362, filed Mar. 6, 2017, which is herein incorporated by reference in its entirety. In addition, the Sequence Listing filed electronically herewith is also hereby incorporated by reference in its entirety (File Name: PRIN-53103_ST25.txt; Date Created: Apr. 18, 2019; File Size: 13,878 bytes.)

STATEMENT REGARDING FEDERALLY SPONSORED RESEARCH OR DEVELOPMENT

This invention was made with government support under Grant No. HR0011-17-2-0010 awarded by Defense Advanced Research Projects Agency (DARPA). The government has certain rights in the invention.

BACKGROUND OF THE INVENTION

Cellular function relies on coordinating the thousands of reactions that simultaneously take place within the cell. Cells accomplish this task in large part by spatio-temporally controlling these reactions using diverse intracellular organelles. In addition to classic membrane-bound organelles such as secretory vesicles, mitochondria and the endoplasmic reticulum, cells harbor a variety of membrane-less organelles. Most of these are abundant in both RNA and protein, and are referred to as ribonucleoprotein (RNP) bodies. Among dozens of examples include nuclear bodies such as nucleoli, Cajal bodies, and PML bodies, and cytoplasmic germ granules, stress granules and processing bodies ((Mao et al., 2011), (Anderson and Kedersha, 2009), (Buchan and Parker, 2009), (Handwerger and Gall, 2006)). By impacting a number of RNA processing reactions within cells, these structures appear to play a central role in controlling the overall flow of genetic information, and are also increasingly implicated as crucibles for protein aggregation pathologies ((Li et al., 2013), (Ramaswami et al., 2013)).

From a biophysical standpoint, these structures are remarkable in that they have no enclosing membrane and yet their overall size and shape may be stable over long periods (hours or longer), even while their constituent molecules exhibit dynamic exchange over timescales of tens of seconds (Phair and Misteli, 2000). Moreover, many of these structures have recently been shown to exhibit additional behaviors typical of condensed liquid phases. For example, P granules, nucleoli, and a number of other membrane-less bodies will fuse into a single larger sphere when brought into contact with one another ((Brangwynne et al., 2009), (Brangwynne et al., 2011), (Feric and Brangwynne, 2013)), in addition to wetting surfaces and dripping in response to shear stresses. These observations have led to the hypothesis that membrane-less organelles represent condensed liquid states of RNA and protein that assemble through intracellular phase separation, analogous to the phase transitions of purified proteins long observed in vitro by structural biologists ((Ishimoto and Tanaka, 1977), (Vekilov, 2010)). Consistent with this view, RNP bodies and other membrane-less organelles appear to form in a concentration-dependent manner, as expected for liquid-liquid phase separation ((Brangwynne et al., 2009), (Weber and Brangwynne, 2015), (Nott et al., 2015), (Wippich et al., 2013), (Molliex et al., 2015)). These studies suggest that cells can regulate membrane-less organelle formation by altering proximity to a phase boundary. Movement through such an intracellular phase diagram could be accomplished by tuning concentration or intermolecular affinity, using mechanisms such as posttranslational modification (PTM) and nucleocytoplasmic shuttling.

Recent work has begun to elucidate the molecular driving forces and biophysical nature of intracellular phases. Weak multivalent interactions between molecules containing tandem repeat protein domains appear to play a central role ((Li et al., 2012), (Banjade and Rosen, 2014)). A related driving force is the promiscuous interactions (e.g. electrostatic, dipole-dipole) between segments of conformationally heterogeneous proteins, known as intrinsically disordered protein or intrinsically disordered regions (IDP/IDR, which are typically low complexity sequences, LCS). Hereinafter, the terms intrinsically disordered protein, intrinsically disordered region, an intrinsically disordered protein region are used interchangeably. RNA binding proteins often contain IDRs with the sequence composition biased toward amino acids including R, G, S, and Y, which comprise sequences that have been shown to be necessary and sufficient for driving condensation into liquid-like protein droplets ((Elbaum-Garfinkle et al., 2015), (Nott et al., 2015), (Lin et al., 2015)). The properties of such in vitro droplets have recently been found to be malleable and time-dependent ((Elbaum-Garfinkle et al., 2015), (Zhang et al., 2015), (Weber and Brangwynne, 2012), (Molliex et al., 2015), (Lin et al., 2015), (Xiang et al., 2015), (Patel et al., 2015)), underscoring the role of IDR/LCSs in both liquid-like physiological assemblies and pathological protein aggregates.

Despite these advances, almost all recent studies rely primarily on in vitro reconstitution, due to a lack of tools for probing protein phase behavior within the living cellular context. However, a growing suite of optogenetic tools have been developed to control protein interactions in living cells. The field has primarily focused on precise control over homo- or hetero-dimerization ((Toettcher et al., 2011), (Kennedy et al., 2010), (Levskaya et al., 2009)). But recent work suggests the potential of optogenetics for studying intracellular phases, demonstrating that light-induced protein clustering can be used to activate cell surface receptors (Bugaj et al., 2013), as well as to trap proteins into inactive complexes ((Lee et al., 2014), (Taslimi et al., 2014)).

Thus, a platform which can be used to dynamically modulate intracellular protein interactions, enabling the spatiotemporal control of phase transitions within living cells is highly desirable. This platform could also be used for various biotechnological applications, including protein purification.

BRIEF SUMMARY OF THE INVENTION

The present invention is directed to a platform for reversibly and non-reversibly generating liquid droplets, gels, or protein aggregates inside and outside cells by using nucleation cores, which may be controlled by light. In the present invention, systems and methods are provided for a system of protein constructs which may utilize a photo-activatable or photo-deactivatable interaction between a light sensitive receptor protein on a first protein construct and its cognate partner on a second protein construct in order to control the recruitment of intrinsically disordered proteins onto cores comprised of self-assembling protein subunits (see, e.g., FIG. 4). In this process, self-assembling protein subunits which are part of the first protein construct will self-assemble and form a "core". As each of the self-assembling protein subunits are fused to a light sensitive receptor protein, light may be used to trigger the assembly or possibly disassembly of a structure comprising the light sensitive receptor protein on a first protein construct with a cognate partner of the light sensitive receptor protein on a second protein construct, where the cognate partner is fused to a full length or truncated low complexity or intrinsically-disordered protein (see, e.g., FIG. 5).

Among the many different possibilities contemplated, the self-assembling protein subunit could be a ferritin heavy chain, and the intrinsically disordered region (IDR) can be the N terminal domain of FUS protein. Photo-inducible reversible heterodimerization between the self-assemblying units (e.g., part of the first protein construct) and IDR units (e.g., part of the second protein construct) could utilize, e.g., the engineered blue light sensitive receptor protein iLID and its cognate partner, sspB. One or both of the protein constructs may be advantageously attached to a fluorescent protein marker. It is contemplated that these protein constructs will be configured such that after being introduced into a living cell, exposing the living cell to certain wavelengths of light will induce molecules within the living cell to cluster or nucleate liquid phases, gels, or aggregates including pathological protein aggregates such as amyloid fibers. In embodiments where photo-activation (or deactivation) is not required, it is contemplated that phase separated clusters would be present in cells independent of the presence or absence of light.

The rapid and reversible clustering capabilities of the platform could be exploited for protein purification applications. For that purpose, a target protein intended for purification is fused through a cleavable protein tag to one of the protein constructs, preferably to the IDR containing construct. Transiently inducing clustering by photo-activation will locally enrich target proteins in separate phases. Exploiting the distinctive physical and chemical properties of these phases, for instance density, enables easy and rapid purification, for instance by droplets sedimentation via centrifugation and supernatant removal. Following a first such purification process, the target protein can be cleaved out using specific protease, while the remaining cluster forming constructs are to be removed through a similar second purification process. Further, by selecting certain IDRs, the platform may be configured to allow enrichment of proteins other than one bound to the construct having a light activated protein or their cognate partners, allowing purification of target proteins which are not directly linked to one of the constructs.

Further envisioned is the formation of synthetic organelles by directly immobilizing several enzymes around a self-assembling core comprising the second protein construct and/or indirectly recruiting enzymes into the phase separated environment generated by the self-assembling intrinsically-disordered-proteins modified cores. This means of locally concentrating enzymes may also facilitate catalytic turnover for biosynthesis and biodegradation applications. The method may also advantageously control accessibility of a reactant by tuning solubility within an encapsulating liquid phase.

DETAILED DESCRIPTION OF THE INVENTION

Before the present invention is described in further detail, it is to be understood that the invention is not limited to the particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, a limited number of the exemplary methods and materials are described herein.

It must be noted that as used herein and in the appended claims, the singular forms "a", "an", and "the" include plural referents unless the context clearly dictates otherwise.

Figure 1A:
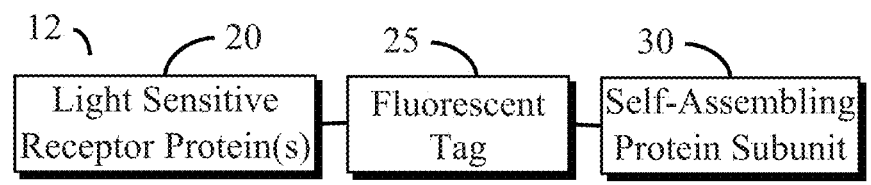
FIGS. 1A, 1B and 1C illustrate embodiments of a platform.
Figure 1A:
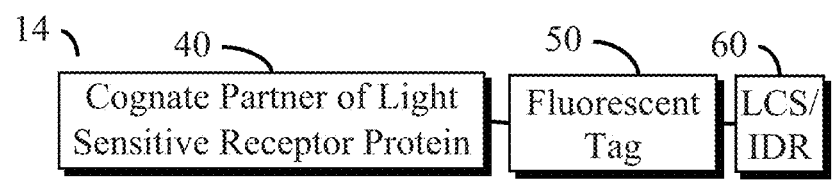
Figure 1B:
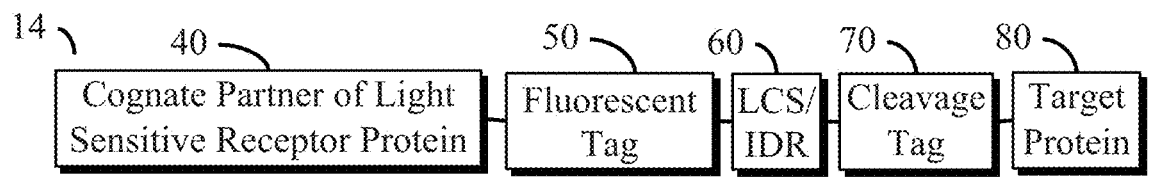

FIGS. 1A and 1B depict generalized embodiments of the disclosed platform. The platform (10) generally comprises two types of protein constructs (12, 14).

The first protein construct (12) comprises at least one light sensitive receptor protein (20) fused to a self-assembling protein subunit (30), which may be an oligomeric protein subunit. Optionally, a fluorescent protein tag (25) may be included, either as indicated in FIG. 1 or other locations if desired. (25).

The at least one light sensitive receptor protein (20) may comprise one or more similar or different proteins responsive to at least one wavelength of light, preferably a wavelength of light in the near UV, visible or infra-red regions, which are from about 350 nm to about 800 nm. In preferred embodiments, the light sensitive protein is the engineered protein iLID, which consist of a modified LOV2 domain fused at its C terminus to an ssrA peptide. In certain embodiments, the self-assembling protein subunit is fused to two or more LOV2-ssrA proteins. However, other light sensitive proteins may also be utilized, including Cry2, PhyB or a LOV2 domain fused to a signaling peptide other than ssrA. The self-assembling protein subunit (30) can be any protein that self-assembles, including but not limited to ferritin light chains, ferritin heavy chains, glutamine synthetase, and viral capsid structure proteins, or synthetic engineered self-assembling proteins. One preferred embodiment utilizes ferritin heavy chain subunits, which are capable of self-assembly into a 24 mer complex with a spherical shell structure. Assembled ferritin form deposits of iron-oxide at its internal cavity. By performing certain mutations, such deposits can become ferrimagnetic, thereby making modified ferritin responsive to magnetic field.

The optional fluorescent protein tag (25) can comprise any appropriate fluorescent protein tag, such as mCherry, although the use of other fluorescent proteins is also envisioned, including but not limited to GFP variants.

The second protein construct (14) comprises at least one cognate partner (40) of the light sensitive receptor protein (20), fused to a full length or truncated low complexity sequence (LCS) or IDR (60). As shown in FIG. 1B, the second construct (14) may also optionally comprise a cleavage tag (70) or a target protein (80). Optionally, a fluorescent tag (50) may be included, either as indicated in FIG. 1B (between the cognate partner and the LCS or IDP) or other locations if desired.

The cognate partner of the light sensitive receptor protein (40) is any appropriate cognate of the light sensitive receptor protein (20), which may include but is not limited to ssrB, Zdk, CIB, or PIF for LOV2-ssrA, LOV2, Cry2, or PhyB respectively. In preferred embodiments, the second protein construct comprises an IDP (60), which include but not limited to full length or truncated forms of FUS [SEQ ID NO.: 1], DDX4 [SEQ ID NO.: 2], and hnRNPA1 [SEQ ID NO.: 3]. In some embodiments, the IDR comprises amino acids 1-214 of FUS, 1-236 of DDX4, or 186-320 of HNRNPA1. The fluorophore (50) can comprise any appropriate fluorescent tag, such as mCherry, although the use of other fluorescent proteins is also envisioned, including but not limited to GFP variants.

When cleavage tags are utilized, at least one cleavage tag (70) is typically inserted between the functional region and a protein (80) that has been targeted for, e.g., purification. A wide variety of cleavage tags are envisioned, including but not limited to: self-cleaving tags, Human Rhinovirus 3C Protease (3C/PreScission), Enterokinase (EKT), Factor Xa (FXa), Tobacco Etch Virus Protease (TEV), and Thrombin (Thr).

Variants of the two types of protein constructs (12, 14) can concomitantly be used, for example, to allow multi-wavelength sensitivity or functionalizing core proteins with different IDRs and/or enzymes.

Figure 1C:
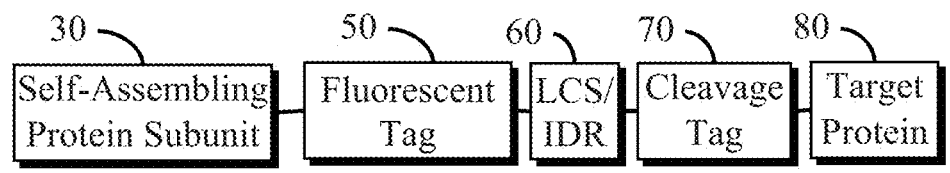

In cases where photo-sensitivity is not necessary, rather than using two constructs to create a photo-activatable or photo-deactivatable systems, a single protein construct (16) may be utilized. As shown in FIG. 1C, the single protein construct could comprise a self-assembling protein subunit (30) and a full length or truncated low complexity sequence (LCS) or IDR (60). Optionally, the single construct could also include at least one of a fluorescent tag (50), a cleavage tag (70), and/or a target protein (80). For example, the single construct (16) could comprise a Ferritin protein fused to the FUS IDR. In this manner, the system could generate a disordered protein-based seed for molecular clustering without requiring photo-activation or -deactivation.

Figure 2A:
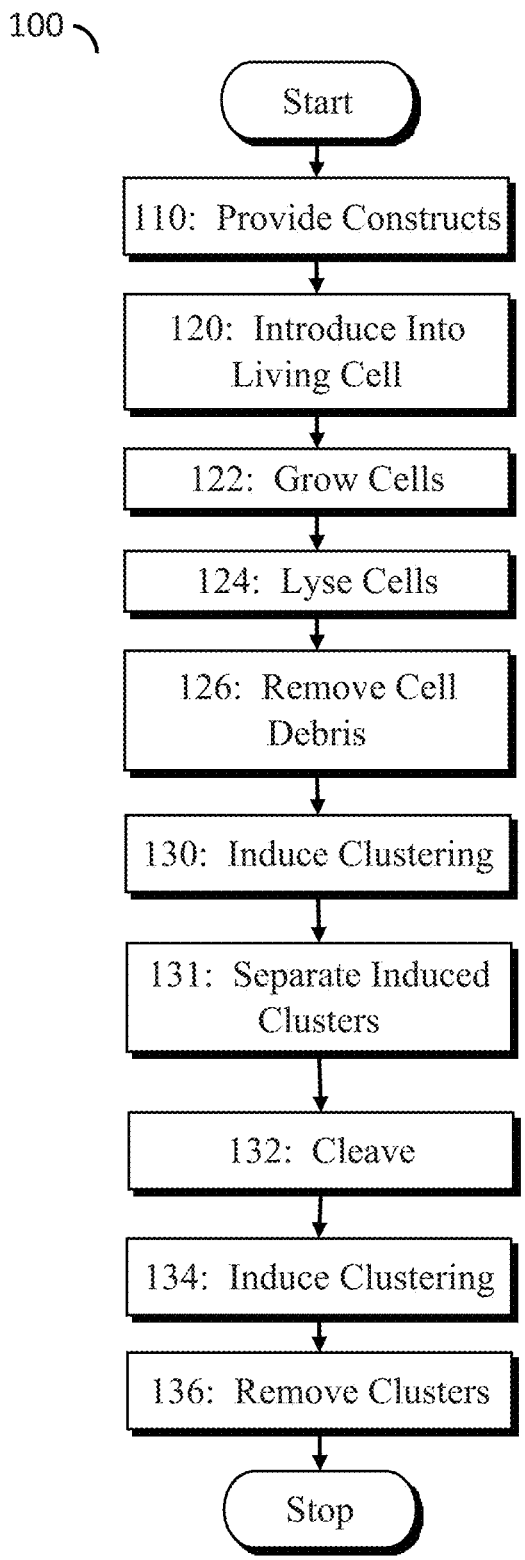
FIGS. 2A, 2B, and 3 are flowcharts of methods utilizing the platform.
Figure 2B:
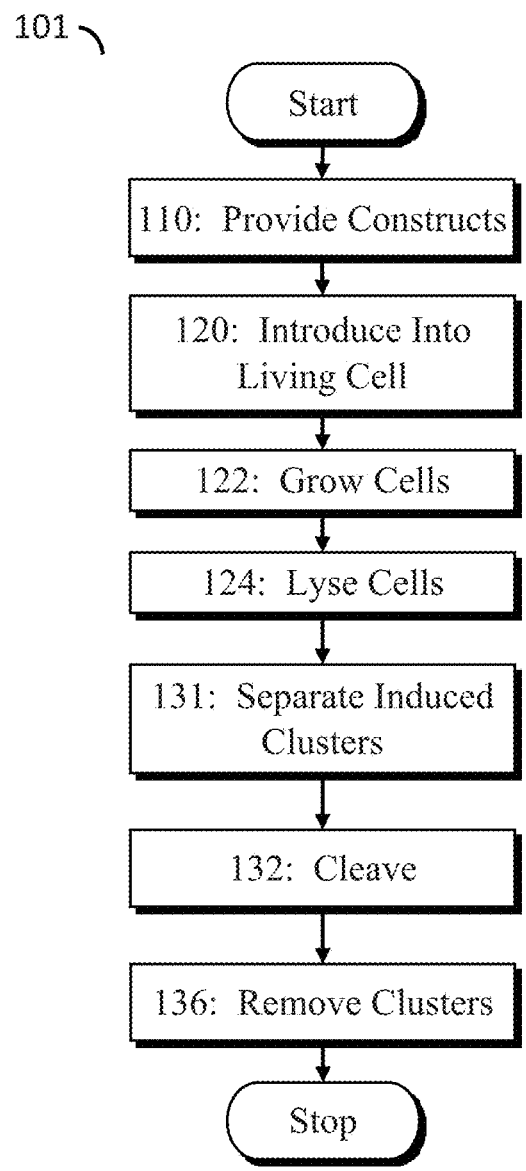

FIG. 2A depicts a flowchart of a method (100) for inducing clusters, which may be used for, e.g., protein purification. FIG. 2B shows the analogous method (101) when utilizing a single non-activatable construct (16). The method generally comprises at least nine steps (six for the single construct). The first step is providing (110) DNA encoding first and second protein constructs (12, 14) as described above, where the second protein construct (14) also encodes a target protein (see, e.g., FIG. 1B, element 80). Alternatively a single light insensitive construct (16) encoding self-assemblying subunit, IDR, and a target protein can be used (see, e.g., FIG. 1C). The DNA encoding the constructs (12 and 14, or 16) is introduced (120) into living cells. Cells are grown (122) and protein production is induced until cells reach desirable density. Cells are then lysed (124) and if photo-activatable or -deactivatable constructs are utilized, the lysate is, e.g., centrifuged (126) to remove larger cell debris. If photo-activatable or -deactivatable constructs are utilized, supernatant is then exposed to at least one wavelength of light (130) that the light sensitive proteins are responsive to, which induces molecules previously within the living cell to cluster or uncluster. As discussed above, the wavelength of light is predetermined, based on the specific wavelengths to which the light sensitive protein utilized in the constructs is responsive. It is noted that for increasing yield, clustering by photoactivation may be applied prior and during the cell lysis step, during which both self-assemblying proteins and target protein constructs are still highly concentrated inside the cells. It is also noted that clustering may also confine additional target proteins or RNA molecules, which are not directly linked to the second protein construct, but help solubilize in the assembled phase and therefore can be purified even in the absence of the cognate partner of the light activatable protein.

The induced clusters may then be separated (131), typically via centrifuge or using a magnetic field, in order to remove, e.g., the unclustered phase. The pellet is resuspended and followed by a cleavage step (132), where the target protein is cleaved from, for example, the IDR (60). If photo-activatable or -deactivatable constructs are utilized, then after cleaving, a second induction step (134) is utilized concomitantly with removing clusters (136) via centrifugation or an applied magnetic field in order to induce clustering of the core construct (12) and the truncated cognate construct, thus leaving the target protein concentrated in the supernatant, which is then able to be collected. If a single construct is used, the second induction step (134) is not utilized, but the clusters are removed (136) following the cleaving step (132).

Figure 3:
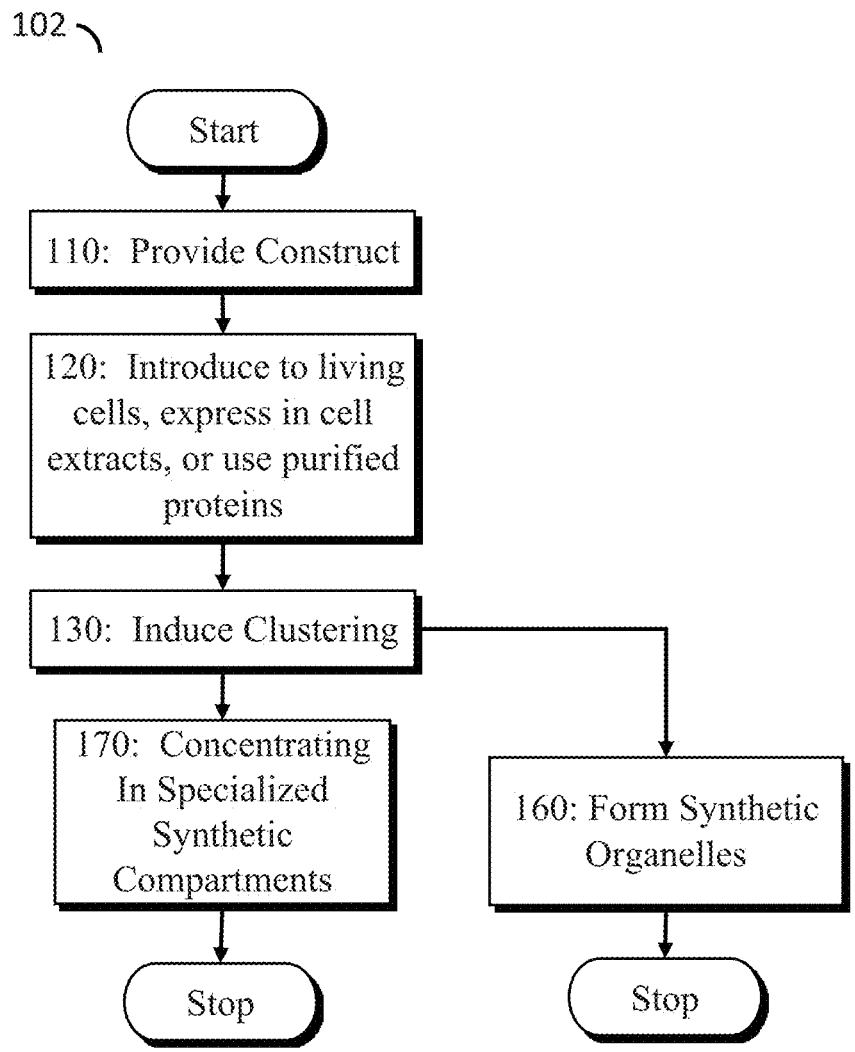

As shown in FIG. 3, the method (102) can be further modified. For example, the method can be modified to form intracellular synthetic organelles (160) by either directly immobilizing several enzymes of a related biochemical pathway around the core of self-assembling protein subunits comprising a plurality of first protein constructs (12), and/or by indirectly recruiting such enzymes into the phase separated environment generated by the self-assembling LCS or IDR modified cores. For the former, a subset of the self-assembling protein subunits may be fused to enzymes, while another subset are fused to light-activatable proteins, or fusions of the self-assembling protein subunits to both enzymes and light-activated proteins may be utilized. For the latter, enzymes may be recruited to the phase separated environment through interactions mediated through, e.g., fusion with peptides/proteins that promote interactions with components of the condensed phase (e.g., fusion of an enzyme to a segment of the FUS IDR, or to an engineered peptide designed to target the enzyme to the condensed phase).

The method and system can also be used to facilitate catalytic turnover upon photo-activation by locally concentrating enzymes in specialized biochemically reactive compartments inside or outside cells (170), for instance for intracellular production of biofuels. And the method can also be used to control accessibility of a reactant by tuning solubility within an encapsulating liquid phase comprising the intrinsically-disordered protein. In preferred embodiments, the concentration (170) follows inducing an additional protein—one not bound to the second construct—to cluster.

As these constructs are modular, properties can be varied, including activation/deactivation times, wavelength sensitivity, core size, light sensitive receptor protein density on the core, IDR sequences, and reversibility.

Figure 4:
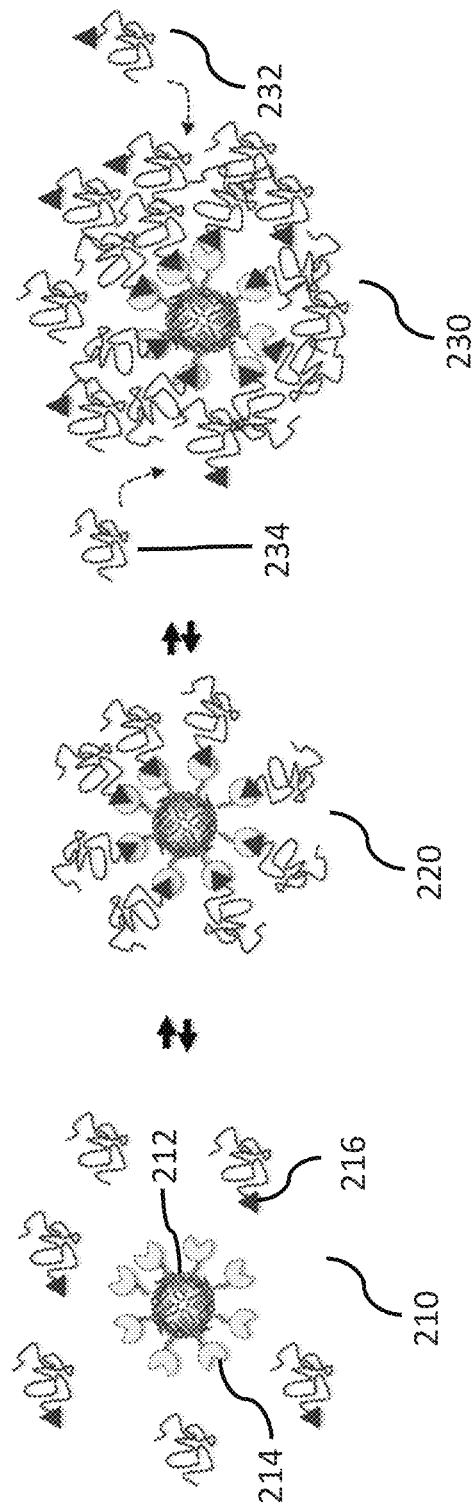
FIGS. 4 and 5 are graphical depiction of the method.

FIG. 4 provides a graphical depiction of the method. In the non-activated configuration (210), a core can be seen, comprising the self-assembling protein subunits (212) of a number of first protein constructs, each self-assembling protein subunit (212) fused to a light sensitive receptor protein (214). One example of a light sensitive receptor protein is a LOV2-ssrA domain. The second protein constructs remain unbound from the core, each second protein construct comprising the cognate partner (216) of the light sensitive protein (here, the cognate partner of the LOV2-ssrA domain is sspB) fused to full length or truncated low complexity or intrinsically-disordered protein (e.g., FUS, etc.).

In the active state (e.g., upon photoactivation), the light sensitive receptor protein (214) binds to the cognate partner (216) of the light sensitive receptor protein. In this example, the buried ssrA peptides become uncaged. Exposed ssrA rapidly bind their cognate sspB partners. Because the cognate partners (216) are bound to an LCS/IDR, the clustering of LCS/IDR around the self-assembled core leads to the formation of a photo-stabilized liquid droplet (220).

Figure 5:
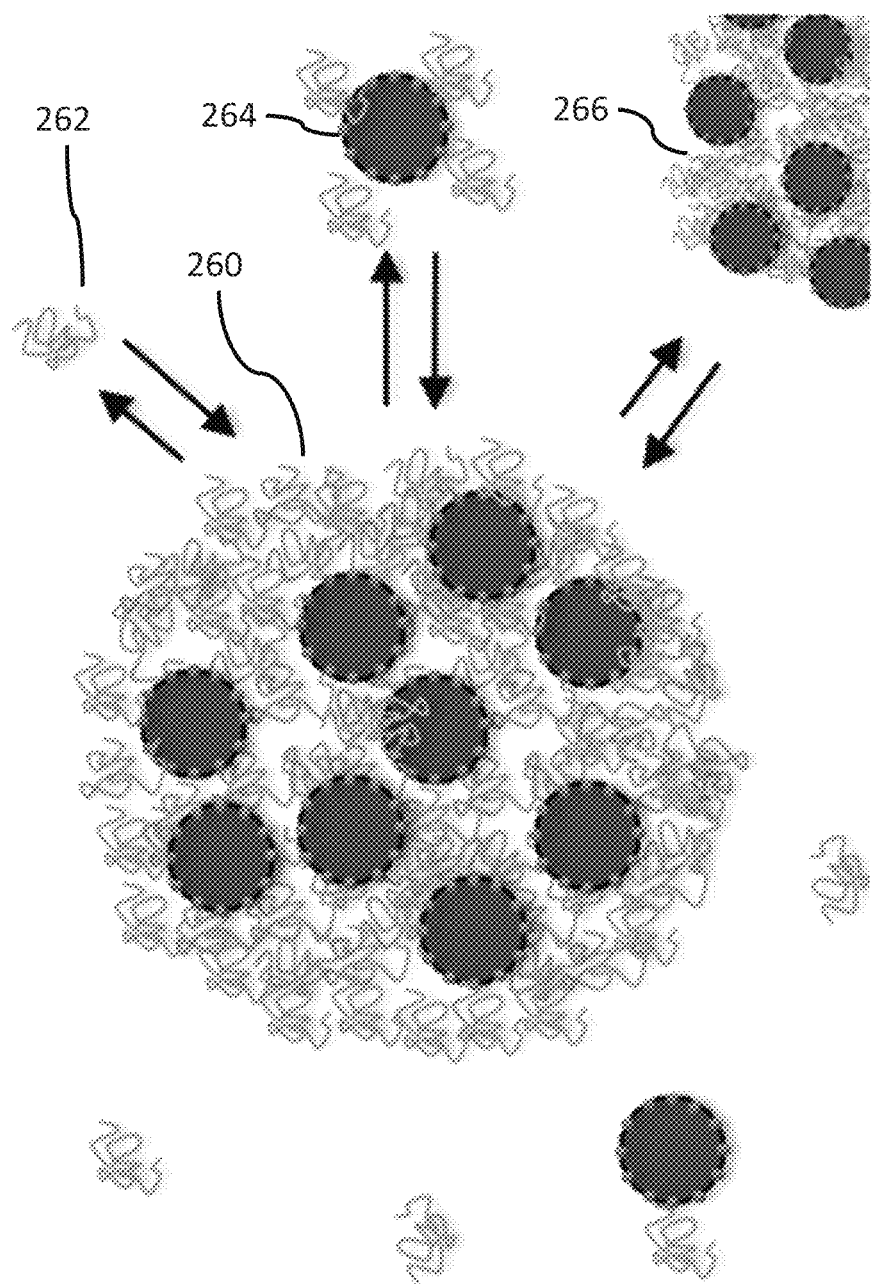

The phase-stabilized liquid droplet (220) may continue to grow to a larger phase-stabilized liquid droplet (230) by recruiting single molecules, such as additional second constructs (232), or endogenous LCS/IDRs (234, 262) or other proteins not fused to a cognate partner. And as shown in FIG. 5, the phase-stabilized liquid droplet (220) may also continue to grow via addition of single proteins (262), single core particles (264), or coalescence of mature multi-core particles (266).

Figure 6:
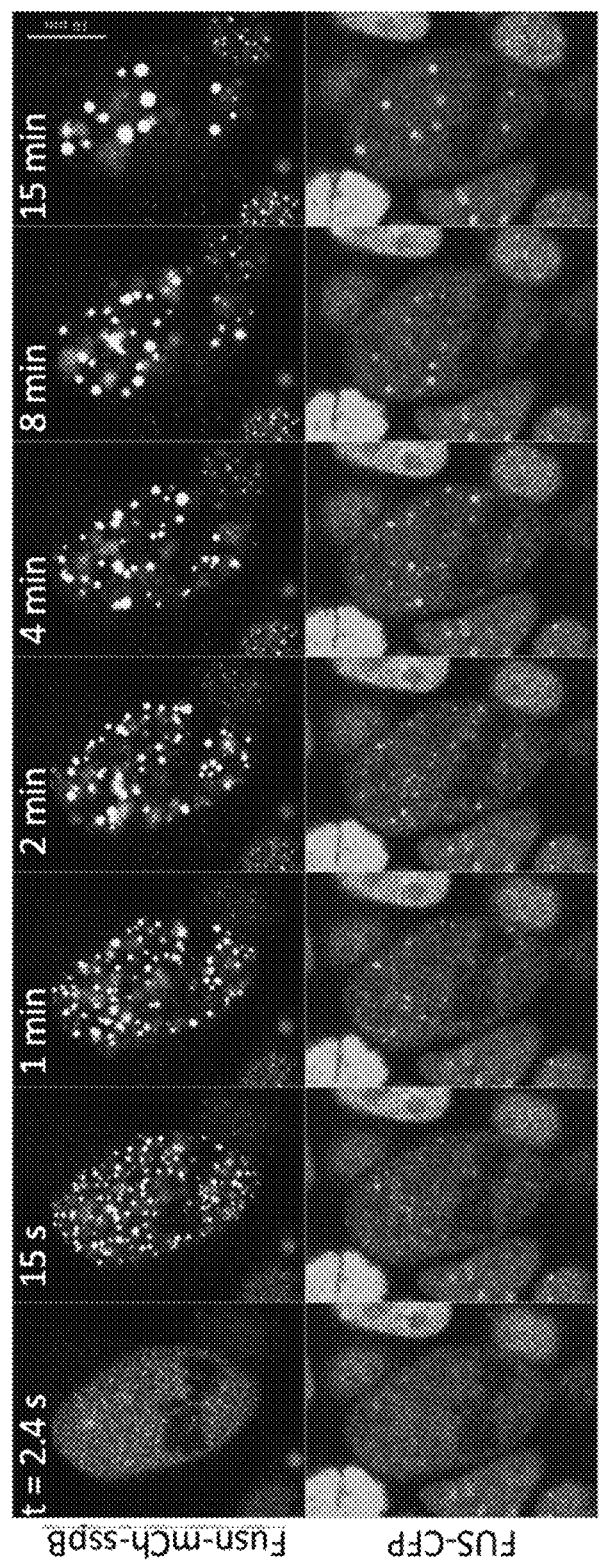
FIG. 6 is a series of images illustrating the recruitment endogenous proteins around cores over time.

An example of recruitment of FUS proteins by core based droplets can be seen by utilizing a first construct comprising ferritin fused to two iLID-ssrA domains, and a second construct comprising FUSn fused to mCherry and sspB. In addition, the system utilizes a full length FUS fused to Cyan Fluorescent Protein (CFP). In this system, as shown in FIG. 6, significant mCherry fluorescence is seen as early as 15 seconds after activation, and CFP fluorescence near the core based droplets starts to appear around that time. As the core droplets grow and coalesce, CFP continues to be recruited, and after 15 minutes of irradiation, significant CFP recruitment can be seen around the cores.

In this example, DNA fragments for human FUS, FUSn (residues 1-214) and human ferritin (heavy chain) were amplified by PCR using HeLa cell's template cDNA. DNA fragments for iLID-ssrA, an engineered protein that is based on *Avena Sativa* LOV2 domain fused to *E. coli* ssrA peptide, and *E. coli* sspB were amplified by PCR (Phusion® high-fidelity DNA polymerase, ThermoFisher Scientific) using PLL7.0:Venus-iLID-Mito (Add gene #60413) and PLL7.0:tgRFPt-SSPB WT (Add gene #60415) respectively. A nuclear localization signal from *Gallus gallus* ferritoid (18 aa encoding 54 bases) was fused to the N terminus of iLID by sequential PCRs.

pHR:NLS-iLID-GFP-ferritin, pHR:NLS-iLID-iLID-GFP-ferritin, pHR:FUS(1-214)-mCherry-sspB, pHR:mCherry-sspB, pHR:FUS-CFP, pHR: DDX4(1-236)-mCherry-sspB and HNRNPA1(186-320)-mCherry-sspB plasmids were constructed using lenti viral pHR backbone through In-Fusion cloning of multiple inserts (In-Fusion® HD Cloning Plus HD cloning kit, Takara Bio USA).

To produce stable cell lines, lentiviral constructs were transiently transfected with FuGENE® HD transfection reagent (Promega), following the manufacturer's recommended protocol, into HEK293T cells. Viruses were harvested 48 hr after transfection and passed through a 0.45-μm filter to remove cell debris. NIH 3T3 cells plated at ~30% confluency in 6-well dishes were infected with NLS-iLID-GFP-ferritin or NLS-iLID-iLID-GFP-ferritin containing viruses by adding 1 mL of filtered viral supernatant directly to the cell medium. Viral medium was replaced with normal growth medium 24 hr after infection. A second construct, FUS-mCherry-sspB or mCherry-sspB, was subsequently added to the ferritin expressing cells following two cell passages.

35-mm glass-bottom dishes were coated for 20 min with 0.25 mg/ml fibronectin and then washed twice with phosphate buffered saline (PBS pH 7.4, Thermo). Cells were plated on the fibronectin-coated dish and grown typically overnight in normal growth medium to reach ~50% confluency. All live cell imaging was performed using 60× oil immersion objective (NA 1.4) on a Nikon A1 laser scanning confocal microscope equipped with a stage top incubator (okolab) set to 37° C. and 20% $CO_2$.

For global activation, cells were irradiated with a 488 nm laser while imaging was conducted using two wavelength (488 nm for GFP-ferritin based constructs and 560 nm for mCherry-sspB based constructs). For executing an activation-deactivation cycle, we typically used a 30-120 s dual wavelength excitation for iLID activation and GFP and mCherry imaging, which was followed by 2-5 min of 560 nm imaging for iLID deactivation. For recruitment assay, iLID was activated simultaneously with FUS-CFP imaging using 450 nm laser excitation, while mCherry was imaged using 513 nm laser excitation.

For local activation, cells were excited by setting the 488 nm laser to scan a confined spherical or line-shape ROIs (0.3-1 μm in diameter/width), while imaging was conducted through the mCherry excitation/readout channel only. Local activation for Fluorescence recovery after photobleaching (FRAP) experiments was conducted by scanning a ring-shape region of interest (ROI) with 488 nm laser, while bleaching of mCherry was performed at the center pixel of the ring using a 560 nm laser.

Figure 7:
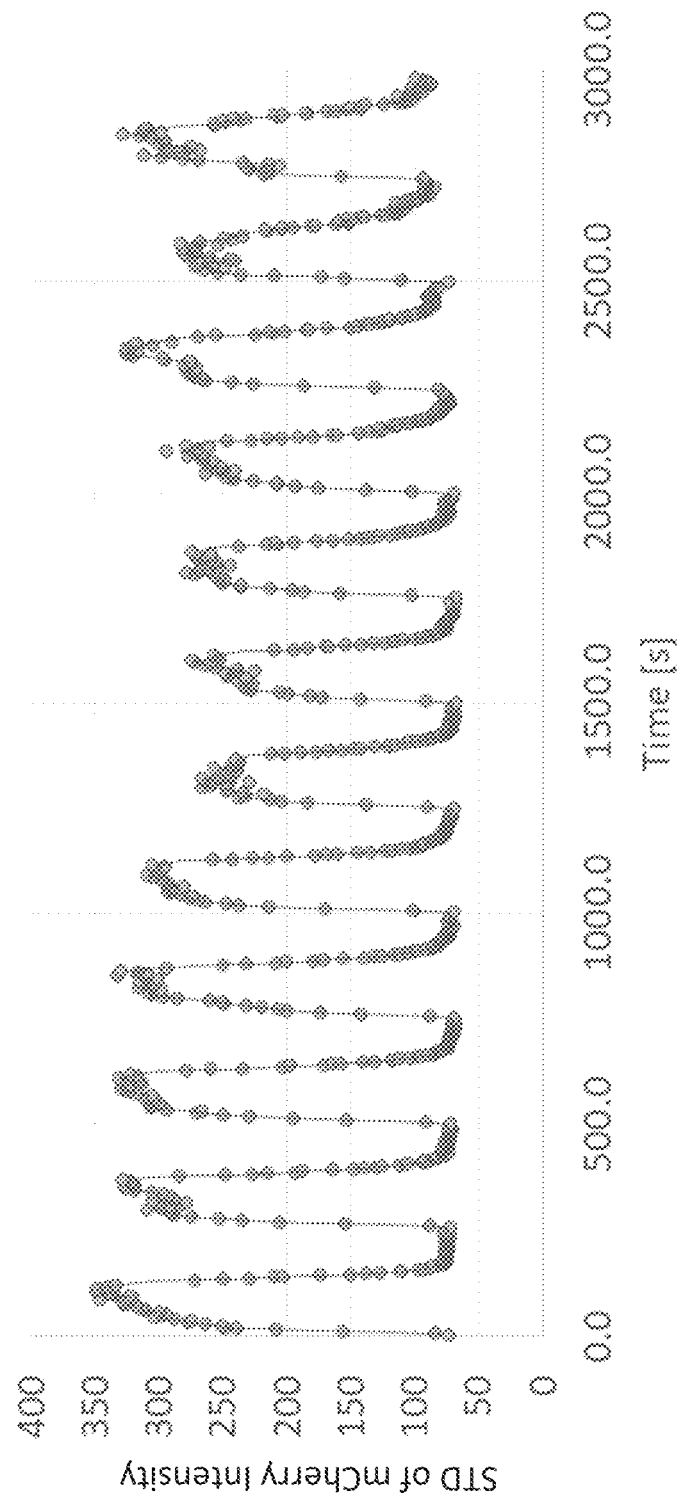
FIG. 7 is a graph illustrating the kinetics and reversibility of the platform.

FIG. 7 illustrates this platform's kinetics and reversibility. FIG. 7 depicts the standard deviation (Std) of mCherry fluorescence intensity of the IDR-sspB construct over a number of activation and deactivation cycles. Change in Std indicates spacial redistribution of fluorophores from a uniform diffusive state to a nonuniform clustered state. For this, a first construct comprising Ferritin fused to LOV2-ssrA and a second construct comprising FUSn fused to sspB. In this example, droplets were observed after is of activation, and dissembling after less than 1 min with an exponential decay half-life of about 11 sec. As indicated in FIG. 6, the Std of Fluorescence indicates rapid kinetics, and a high degree of reversibility. When two or more LOV2-ssrA domains were utilized, however, irreversible droplets were seen after three cycles of activation and deactivation.

Figures 8A, 8B:
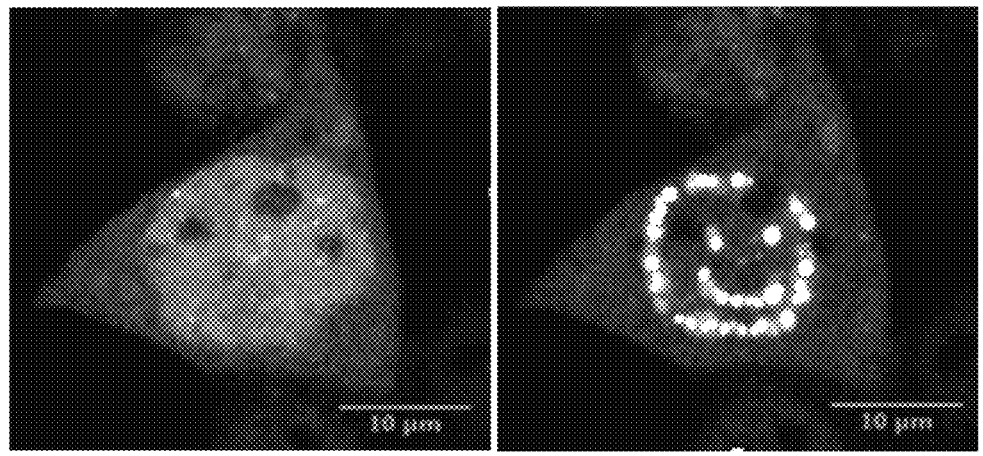
FIGS. 8A and 8B are images of a cell before and after certain areas of the cell were irradiated.
Figure 8C:
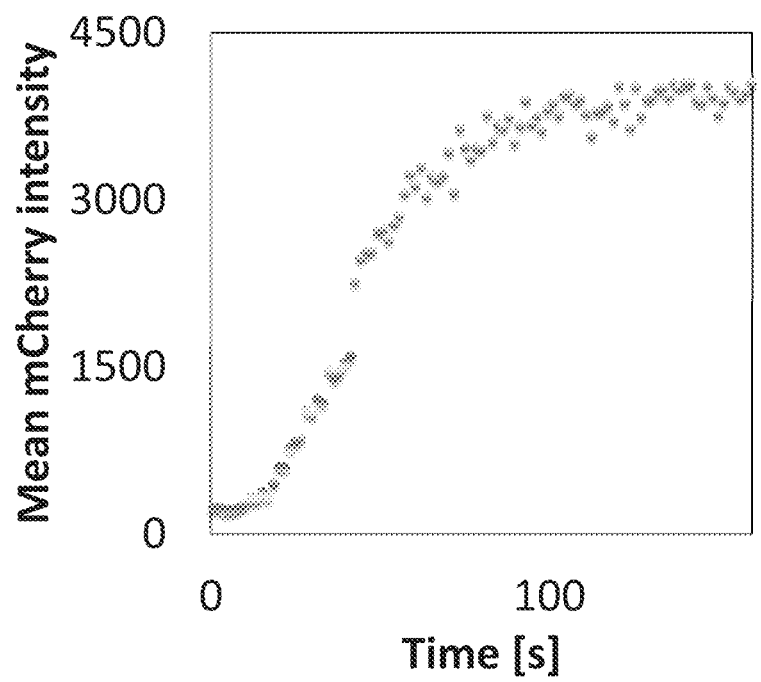
FIG. 8C is a graph illustrating the concentration capability of the platform.

FIGS. 8A-C illustrate some of the potential of the droplet's ability to concentrate, e.g., the disclosed protein constructs in a single intracellular cluster. FIG. 8A shows a cell comprising one example of a particular system before being irradiated. This system utilized a first construct comprising Ferritin fused to LOV2-ssrA and a second construct comprising FUSn fused to mCherry and sspB. Rather than irradiating the entire cell, specific small areas of the cell were irradiated, each area approximately 1 micrometer in diameter. FIG. 8B shows the patterned activation of multiple single droplets within the cell, each bright droplet indicating a region where the proteins are concentrated. FIG. 8C shows the mean mCherry intensity over time for the particular system, which is an relative measure of protein concentration. As shown in FIG. 8C, the droplets formed were 100-fold more concentrated than nucleoplasm.

Kits may also be provided to simplify the use of these methods. The kits will generally include plasmids for the two protein constructs (12, 14) or a single construct (16) as described above, as well as at least one light emitting device that can be used to activate or deactivate the light sensitive proteins. Kits may also include a microfabricated device for activation and collection of condensed liquid phases.

Thus, specific devices and systems for nucleated protein clustering have been disclosed. It should be apparent, however, to those skilled in the art that many more modifications besides those already described are possible without departing from the inventive concepts herein. The inventive subject matter, therefore, is not to be restricted except in the spirit of the disclosure. Moreover, in interpreting the disclosure, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

The invention claimed is:

1. A composition comprising a plurality of fusion proteins, wherein each fusion protein of the plurality of fusion proteins comprising at least one self-assembling protein, a full-length or truncated low complexity or intrinsically disordered protein region, and a target protein,
   wherein the at least one self-assembling protein and the low complexity or intrinsically disordered protein region are heterologous,
   wherein the target protein is attached to a C-terminus of the low complexity or intrinsically disordered protein region, and
   wherein the plurality of fusion proteins are configured to form phase separated clusters.

2. The composition according to claim 1, wherein the self-assembling protein is ferritin.

3. The composition according to claim 2, wherein the ferritin is a ferritin heavy or light chain.

4. The composition according to claim 1, wherein the low complexity or intrinsically disordered protein region is selected from the group consisting of FUS or FUSn.

5. The composition according to claim 1, further comprising a fluorescent tag.

6. The composition according to claim 1, further comprising a cleavage tag.

7. The composition according to claim 6, wherein the cleavage tag is selected from the group consisting of: Human Rhinovirus 3C Protease (3C/PreScission), Enterokinase (EKT), Factor Xa (FXa), Tobacco Etch Virus Protease (TEV), and Thrombin (Thr).

8. The composition according to claim 6, wherein the cleavage tag is a self-cleaving tag.

9. A cell line that is capable of expressing a plurality of fusion proteins, wherein each fusion protein of the plurality of fusion proteins comprising at least one self-assembling protein, a full-length or truncated low complexity or intrinsically disordered protein region, and a target protein,
   wherein the at least one self-assembling protein and the low complexity or intrinsically disordered protein region are heterologous,
   wherein the target protein is attached to a C-terminus of the low complexity or intrinsically disordered protein region.

10. A method for forming phase separated clusters in a living cell, comprising the steps of:
    expressing within a living cell, a plurality of fusion proteins, wherein each fusion protein of the plurality of fusion proteins comprising at least one self-assembling protein, a full-length or truncated low complexity or intrinsically disordered protein region, and a target protein,
    wherein the at least one self-assembling protein and the low complexity or intrinsically disordered protein region are heterologous,
    wherein the target protein is attached to a C-terminus of the low complexity or intrinsically disordered protein region; and
    allowing the plurality of fusion proteins to undergo phase separation into at least one condensed phase within the living cell, the at least one condensed phase comprising the plurality of fusion proteins, and form at least one phase separated cluster.

11. The method according to claim 10, wherein the condensed phase in the living cell further comprises amyloid fibers.

12. The method according to claim 10, wherein the fusion proteins further comprises a cleavage tag.

13. The method according to claim 12, wherein the cleavage tag is selected from the group consisting of: Human Rhinovirus 3C Protease (3C/PreScission), Enterokinase (EKT), Factor Xa (FXa), Tobacco Etch Virus Protease (TEV), and Thrombin (Thr).

14. The method according to claim 12, wherein the cleavage tag is a self-cleaving tag.

15. The method according to claim 10, wherein the at least one phase separated cluster has a diameter of at least 0.3 micrometer.

16. The method according to claim 10, wherein the fusion proteins are present in the at least one phase separated cluster in a first concentration, the fusion proteins are present outside the at least one phase separated cluster in a second concentration, the first concentration being at least 100 times greater than the second concentration.

* * * * *

UNITED STATES PATENT AND TRADEMARK OFFICE
CERTIFICATE OF CORRECTION

Page 1 of 1

PATENT NO. : 11,053,492 B2
APPLICATION NO. : 16/704115
DATED : July 6, 2021
INVENTOR(S) : Brangwynne et al.

It is certified that error appears in the above-identified patent and that said Letters Patent is hereby corrected as shown below:

In the Specification

Column 1, Line 7, replace the following:
"This application claims priority to U.S. Provisional Application No. 62/467,362, filed March 6, 2017, which is herein incorporated by reference in its entirety. In addition, the Sequence Listing filed electronically herewith is also hereby incorporated by reference in its entirety (File Name: PRIN-53103_ST25.txt; Date Created: April 18, 2019; File Size: 13,878 bytes.)."
With:
--This application is a divisional of application No. 15/618,361, filed on June 9, 2017, now Pat. No. 10,538,756, and claims priority to U.S. Provisional Application No. 62/467,362, which is herein incorporated by reference its entirety.--

Column 1, Line 14, insert the following:
--REFERENCE TO SEQUENCE LISTING SUBMITTED ELECTRONICALLY
The Sequence Listing filed electronically herewith is also hereby incorporated by reference in its entirety (File Name: PRIN-53103_ST25.txt; Date Created: April 18, 2019; File Size: 13,878 bytes.)--

Signed and Sealed this
Twenty-second Day of February, 2022

Drew Hirshfeld
*Performing the Functions and Duties of the
Under Secretary of Commerce for Intellectual Property and
Director of the United States Patent and Trademark Office*

SEQUENCE LISTING

```
<160> NUMBER OF SEQ ID NOS: 3

<210> SEQ ID NO 1
<211> LENGTH: 526
<212> TYPE: PRT
<213> ORGANISM: Homo sapiens

<400> SEQUENCE: 1

Met Ala Ser Asn Asp Tyr Thr Gln Gln Ala Thr Gln Ser Tyr Gly Ala
1               5                   10                  15

Tyr Pro Thr Gln Pro Gly Gln Gly Tyr Ser Gln Gln Ser Ser Gln Pro
            20                  25                  30

Tyr Gly Gln Gln Ser Tyr Ser Gly Tyr Ser Gln Ser Thr Asp Thr Ser
        35                  40                  45

Gly Tyr Gly Gln Ser Ser Tyr Ser Ser Tyr Gly Gln Ser Gln Asn Thr
    50                  55                  60

Gly Tyr Gly Thr Gln Ser Thr Pro Gln Gly Tyr Gly Ser Thr Gly Gly
65                  70                  75                  80

Tyr Gly Ser Ser Gln Ser Ser Gln Ser Ser Tyr Gly Gln Gln Ser Ser
                85                  90                  95

Tyr Pro Gly Tyr Gly Gln Gln Pro Ala Pro Ser Ser Thr Ser Gly Ser
            100                 105                 110

Tyr Gly Ser Ser Ser Gln Ser Ser Tyr Gly Gln Pro Gln Ser Gly
        115                 120                 125

Ser Tyr Ser Gln Gln Pro Ser Tyr Gly Gly Gln Gln Gln Ser Tyr Gly
    130                 135                 140

Gln Gln Gln Ser Tyr Asn Pro Pro Gln Gly Tyr Gly Gln Gln Asn Gln
145                 150                 155                 160

Tyr Asn Ser Ser Ser Gly Gly Gly Gly Gly Gly Gly Gly Gly Asn
                165                 170                 175

Tyr Gly Gln Asp Gln Ser Ser Met Ser Ser Gly Gly Gly Ser Gly Gly
            180                 185                 190

Gly Tyr Gly Asn Gln Asp Gln Ser Gly Gly Gly Gly Ser Gly Gly Tyr
        195                 200                 205

Gly Gln Gln Asp Arg Gly Gly Arg Gly Arg Gly Gly Ser Gly Gly Gly
    210                 215                 220

Gly Gly Gly Gly Gly Gly Gly Tyr Asn Arg Ser Ser Gly Gly Tyr Glu
```

```
            225                 230                 235                 240

Pro Arg Gly Arg Gly Gly Arg Gly Arg Gly Gly Met Gly Gly
                245                 250                 255

Ser Asp Arg Gly Gly Phe Asn Lys Phe Gly Gly Pro Arg Asp Gln Gly
                260                 265                 270

Ser Arg His Asp Ser Glu Gln Asp Asn Ser Asp Asn Thr Ile Phe
                275                 280                 285

Val Gln Gly Leu Gly Glu Asn Val Thr Ile Glu Ser Val Ala Asp Tyr
        290                 295                 300

Phe Lys Gln Ile Gly Ile Ile Lys Thr Asn Lys Lys Thr Gly Gln Pro
305                 310                 315                 320

Met Ile Asn Leu Tyr Thr Asp Arg Glu Thr Gly Lys Leu Lys Gly Glu
                325                 330                 335

Ala Thr Val Ser Phe Asp Asp Pro Pro Ser Ala Lys Ala Ala Ile Asp
                340                 345                 350

Trp Phe Asp Gly Lys Glu Phe Ser Gly Asn Pro Ile Lys Val Ser Phe
                355                 360                 365

Ala Thr Arg Arg Ala Asp Phe Asn Arg Gly Gly Gly Asn Gly Arg Gly
                370                 375                 380

Gly Arg Gly Arg Gly Gly Pro Met Gly Arg Gly Gly Tyr Gly Gly Gly
385                 390                 395                 400

Gly Ser Gly Gly Gly Gly Arg Gly Gly Phe Pro Ser Gly Gly Gly Gly
                405                 410                 415

Gly Gly Gly Gln Gln Arg Ala Gly Asp Trp Lys Cys Pro Asn Pro Thr
                420                 425                 430

Cys Glu Asn Met Asn Phe Ser Trp Arg Asn Glu Cys Asn Gln Cys Lys
                435                 440                 445

Ala Pro Lys Pro Asp Gly Pro Gly Gly Pro Gly Gly Ser His Met
                450                 455                 460

Gly Gly Asn Tyr Gly Asp Asp Arg Arg Gly Gly Arg Gly Gly Tyr Asp
465                 470                 475                 480

Arg Gly Gly Tyr Arg Gly Arg Gly Gly Asp Arg Gly Gly Phe Arg Gly
                485                 490                 495

Gly Arg Gly Gly Gly Asp Arg Gly Gly Phe Gly Pro Gly Lys Met Asp
                500                 505                 510

Ser Arg Gly Glu His Arg Gln Asp Arg Arg Glu Arg Pro Tyr
                515                 520                 525

<210> SEQ ID NO 2
<211> LENGTH: 724
<212> TYPE: PRT
<213> ORGANISM: Homo sapiens

<400> SEQUENCE: 2

Met Gly Asp Glu Asp Trp Glu Ala Glu Ile Asn Pro His Met Ser Ser
1               5                   10                  15

Tyr Val Pro Ile Phe Glu Lys Asp Arg Tyr Ser Gly Glu Asn Gly Asp
                20                  25                  30

Asn Phe Asn Arg Thr Pro Ala Ser Ser Ser Glu Met Asp Asp Gly Pro
        35                  40                  45

Ser Arg Arg Asp His Phe Met Lys Ser Gly Phe Ala Ser Gly Arg Asn
    50                  55                  60

Phe Gly Asn Arg Asp Ala Gly Glu Cys Asn Lys Arg Asp Asn Thr Ser
65                  70                  75                  80
```

-continued

```
Thr Met Gly Gly Phe Gly Val Gly Lys Ser Phe Gly Asn Arg Gly Phe
                 85                  90                  95
Ser Asn Ser Arg Phe Glu Asp Gly Asp Ser Ser Gly Phe Trp Arg Glu
            100                 105                 110
Ser Ser Asn Asp Cys Glu Asp Asn Pro Thr Arg Asn Arg Gly Phe Ser
        115                 120                 125
Lys Arg Gly Gly Tyr Arg Asp Gly Asn Asn Ser Glu Ala Ser Gly Pro
    130                 135                 140
Tyr Arg Arg Gly Gly Arg Gly Ser Phe Arg Gly Cys Arg Gly Gly Phe
145                 150                 155                 160
Gly Leu Gly Ser Pro Asn Asn Asp Leu Asp Pro Asp Glu Cys Met Gln
                165                 170                 175
Arg Thr Gly Gly Leu Phe Gly Ser Arg Arg Pro Val Leu Ser Gly Thr
            180                 185                 190
Gly Asn Gly Asp Thr Ser Gln Ser Arg Ser Gly Ser Gly Ser Glu Arg
        195                 200                 205
Gly Gly Tyr Lys Gly Leu Asn Glu Glu Val Ile Thr Gly Ser Gly Lys
    210                 215                 220
Asn Ser Trp Lys Ser Glu Ala Glu Gly Gly Glu Ser Ser Asp Thr Gln
225                 230                 235                 240
Gly Pro Lys Val Thr Tyr Ile Pro Pro Pro Pro Glu Asp Glu Asp
                245                 250                 255
Ser Ile Phe Ala His Tyr Gln Thr Gly Ile Asn Phe Asp Lys Tyr Asp
            260                 265                 270
Thr Ile Leu Val Glu Val Ser Gly His Asp Ala Pro Pro Ala Ile Leu
        275                 280                 285
Thr Phe Glu Glu Ala Asn Leu Cys Gln Thr Leu Asn Asn Asn Ile Ala
    290                 295                 300
Lys Ala Gly Tyr Thr Lys Leu Thr Pro Val Gln Lys Tyr Ser Ile Pro
305                 310                 315                 320
Ile Ile Leu Ala Gly Arg Asp Leu Met Ala Cys Ala Gln Thr Gly Ser
                325                 330                 335
Gly Lys Thr Ala Ala Phe Leu Leu Pro Ile Leu Ala His Met Met His
            340                 345                 350
Asp Gly Ile Thr Ala Ser Arg Phe Lys Glu Leu Gln Glu Pro Glu Cys
        355                 360                 365
Ile Ile Val Ala Pro Thr Arg Glu Leu Val Asn Gln Ile Tyr Leu Glu
    370                 375                 380
Ala Arg Lys Phe Ser Phe Gly Thr Cys Val Arg Ala Val Val Ile Tyr
385                 390                 395                 400
Gly Gly Thr Gln Leu Gly His Ser Ile Arg Gln Ile Val Gln Gly Cys
                405                 410                 415
Asn Ile Leu Cys Ala Thr Pro Gly Arg Leu Met Asp Ile Ile Gly Lys
            420                 425                 430
Glu Lys Ile Gly Leu Lys Gln Ile Lys Tyr Leu Val Leu Asp Glu Ala
        435                 440                 445
Asp Arg Met Leu Asp Met Gly Phe Gly Pro Glu Met Lys Lys Leu Ile
    450                 455                 460
Ser Cys Pro Gly Met Pro Ser Lys Glu Gln Arg Gln Thr Leu Met Phe
465                 470                 475                 480
Ser Ala Thr Phe Pro Glu Glu Ile Gln Arg Leu Ala Ala Glu Phe Leu
                485                 490                 495
Lys Ser Asn Tyr Leu Phe Val Ala Val Gly Gln Val Gly Gly Ala Cys
```

```
                500                 505                 510
Arg Asp Val Gln Gln Thr Val Leu Gln Val Gly Gln Phe Ser Lys Arg
            515                 520                 525
Glu Lys Leu Val Glu Ile Leu Arg Asn Ile Gly Asp Glu Arg Thr Met
        530                 535                 540
Val Phe Val Glu Thr Lys Lys Ala Asp Phe Ile Ala Thr Phe Leu
545                 550                 555                 560
Cys Gln Glu Lys Ile Ser Thr Thr Ser Ile His Gly Asp Arg Glu Gln
                565                 570                 575
Arg Glu Arg Glu Gln Ala Leu Gly Asp Phe Arg Phe Gly Lys Cys Pro
            580                 585                 590
Val Leu Val Ala Thr Ser Val Ala Ala Arg Gly Leu Asp Ile Glu Asn
                595                 600                 605
Val Gln His Val Ile Asn Phe Asp Leu Pro Ser Thr Ile Asp Glu Tyr
            610                 615                 620
Val His Arg Ile Gly Arg Thr Gly Arg Cys Gly Asn Thr Gly Arg Ala
625                 630                 635                 640
Ile Ser Phe Phe Asp Leu Glu Ser Asp Asn His Leu Ala Gln Pro Leu
                645                 650                 655
Val Lys Val Leu Thr Asp Ala Gln Gln Asp Val Pro Ala Trp Leu Glu
            660                 665                 670
Glu Ile Ala Phe Ser Thr Tyr Ile Pro Gly Phe Ser Gly Ser Thr Arg
        675                 680                 685
Gly Asn Val Phe Ala Ser Val Asp Thr Arg Lys Gly Lys Ser Thr Leu
    690                 695                 700
Asn Thr Ala Gly Phe Ser Ser Gln Ala Pro Asn Pro Val Asp Asp
705                 710                 715                 720
Glu Ser Trp Asp

<210> SEQ ID NO 3
<211> LENGTH: 320
<212> TYPE: PRT
<213> ORGANISM: Homo sapiens

<400> SEQUENCE: 3

Met Ser Lys Ser Ala Ser Pro Lys Glu Pro Glu Gln Leu Arg Lys Leu
1               5                   10                  15
Phe Ile Gly Gly Leu Ser Phe Glu Thr Thr Asp Glu Ser Leu Arg Ser
                20                  25                  30
His Phe Glu Gln Trp Gly Thr Leu Thr Asp Cys Val Val Met Arg Asp
            35                  40                  45
Pro Asn Thr Lys Arg Ser Arg Gly Phe Gly Phe Val Thr Tyr Ala Thr
        50                  55                  60
Val Glu Glu Val Asp Ala Ala Met Asn Thr Thr Pro His Lys Val Asp
65                  70                  75                  80
Gly Arg Val Val Glu Pro Lys Arg Ala Val Ser Arg Glu Asp Ser Gln
                85                  90                  95
Arg Pro Gly Ala His Leu Thr Val Lys Lys Ile Phe Val Gly Gly Ile
            100                 105                 110
Lys Glu Asp Thr Glu Glu His His Leu Arg Asp Tyr Phe Glu Gln Tyr
        115                 120                 125
Gly Lys Ile Glu Val Ile Glu Ile Met Thr Asp Arg Gly Ser Gly Lys
    130                 135                 140
Lys Arg Gly Phe Ala Phe Val Thr Phe Asp Asp His Asp Ser Val Asp
```

-continued

```
145                 150                 155                 160
Lys Ile Val Ile Gln Lys Tyr His Thr Val Lys Gly His Asn Cys Glu
                165                 170                 175

Val Arg Lys Ala Leu Pro Lys Gln Glu Met Ala Ser Ala Ser Ser Ser
                180                 185                 190

Gln Arg Gly Arg Arg Gly Ser Gly Asn Phe Gly Gly Gly Arg Gly Asp
            195                 200                 205

Gly Phe Gly Gly Asn Asp Asn Phe Gly Arg Gly Gly Asn Phe Ser Gly
        210                 215                 220

Arg Gly Gly Phe Gly Gly Ser Cys Gly Gly Gly Gly Tyr Gly Gly Ser
225                 230                 235                 240

Gly Asp Gly Tyr Asn Gly Phe Gly Asn Asp Gly Ser Asn Phe Gly Gly
                245                 250                 255

Gly Gly Ser Tyr Asn Asp Phe Gly Asn Tyr Asn Asn Gln Ser Ser Asn
                260                 265                 270

Phe Gly Pro Met Lys Gly Gly Asn Phe Gly Gly Arg Ser Ser Gly Pro
            275                 280                 285

Tyr Gly Gly Gly Gln Tyr Phe Ala Lys Pro Gln Asn Gln Gly Gly
        290                 295                 300

Tyr Gly Val Ser Ser Ser Ser Ser Ser Tyr Gly Ser Gly Arg Arg Phe
305                 310                 315                 320
```